(12) United States Patent
Sakamoto et al.

(10) Patent No.: US 8,871,977 B2
(45) Date of Patent: Oct. 28, 2014

(54) ASYMMETRIC AZINE COMPOUND AND METHOD FOR PRODUCING THE SAME

(75) Inventors: Kei Sakamoto, Tokyo (JP); Yasushi Nakano, Yonesawa (JP)

(73) Assignee: Zeon Corporation, Tokyo (JP)

( * ) Notice: Subject to any disclaimer, the term of this patent is extended or adjusted under 35 U.S.C. 154(b) by 748 days.

(21) Appl. No.: 12/997,966

(22) PCT Filed: Jun. 17, 2009

(86) PCT No.: PCT/JP2009/061014
§ 371 (c)(1),
(2), (4) Date: Mar. 2, 2011

(87) PCT Pub. No.: WO2010/001726
PCT Pub. Date: Jan. 7, 2010

(65) Prior Publication Data
US 2011/0144379 A1    Jun. 16, 2011

(30) Foreign Application Priority Data

Jun. 30, 2008    (JP) ................. 2008-170743

(51) Int. Cl.
C07C 251/88 (2006.01)
C07C 241/02 (2006.01)
C07C 243/18 (2006.01)
C07C 249/16 (2006.01)

(52) U.S. Cl.
CPC ............. *C07C 251/88* (2013.01); *C07C 249/16* (2013.01)
USPC .......................................... 564/249; 560/250

(58) Field of Classification Search
USPC .......................................... 560/250; 564/249
See application file for complete search history.

(56) References Cited

U.S. PATENT DOCUMENTS

| | | | |
|---|---|---|---|
| 3,829,492 A | 8/1974 | Miller | |
| 4,196,975 A | 4/1980 | Mailer | |
| 4,265,784 A | 5/1981 | Mailer | |
| 4,385,067 A | 5/1983 | Resnick | |
| 6,010,642 A * | 1/2000 | Takatsu et al. ............. | 252/299.6 |
| 2010/0258764 A1 | 10/2010 | Sakamoto | |

FOREIGN PATENT DOCUMENTS

| | | |
|---|---|---|
| JP | 54-87688 | 7/1979 |
| JP | 10-59919 | 3/1998 |
| WO | WO 98/01120 A1 | 1/1998 |
| WO | WO 2008/133290 A1 | 11/2008 |
| WO | WO 2009/041512 A1 | 4/2009 |

OTHER PUBLICATIONS

Dabideen et al., Phenolic Hydrazones Are Potent Inhibitors of Macrophage Migration Inhibitory Factor Proinflammatory Activity and Survival Improving Agents in Sepsis, J. Med. Chem. 50, 1993-1997, 2007.*

M. Negishi, et al.; "Development of Liquid Crystalline Azines for STN-LCD;" DIC Technical Review No. 5; 1999; pp. 17-20 and 10 Sheets of translation (14 sheets total.)/Cited in International Search Report.

International Search Report for International Application No. PCT/JP2009/061014 dated Jul. 31, 2009.

* cited by examiner

Primary Examiner — Johann R Richter
Assistant Examiner — Mark Luderer
(74) Attorney, Agent, or Firm — Kratz, Quintos & Hanson, LLP

(57) ABSTRACT

Disclosed are a novel asymmetric azine compound (I) and a method for producing an asymmetric azine compound (I) which is characterized in that an aldehyde compound (III) and hydrazine are reacted in an alcohol solvent at a molar ratio (aldehyde compound (III)):(hydrazine) of from 2:1 to 1:2, thereby obtaining a reaction solution including a hydrazone compound (IV), and then an aldehyde compound (V) is added for a reaction into the thus-obtained reaction solution at a molar ratio (aldehyde compound (V)):(hydrazone compound (IV)) of from 2:1 to 1:2.

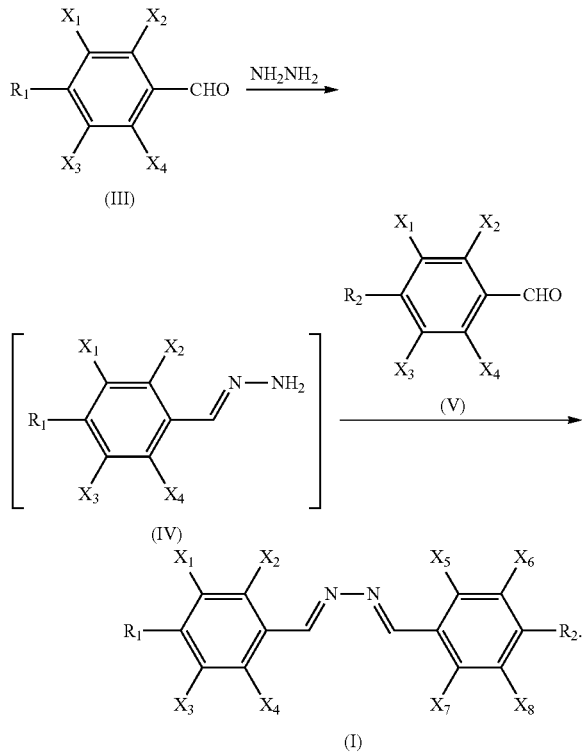

The method can commercially advantageously produce an asymmetric azine compound having a polar group such as a hydroxyl group or a carboxyl group in each molecule. The novel asymmetric azine compound can be obtained by this production method. (In the formulae, $R_1$ and $R_2$ each represents a hydroxyl group or a carboxyl group, $X_1$ to $X_8$ each represents a hydrogen atom, $-C(=O)-OR^3$ or the like; and $R^3$ represents an alkyl group having 1 to 10 carbon atoms or the like.)

4 Claims, No Drawings

ASYMMETRIC AZINE COMPOUND AND METHOD FOR PRODUCING THE SAME

TECHNICAL FIELD

The present invention relates to an asymmetric azine compound that is useful as an intermediate for a liquid crystal compound or the like, and a method of producing the same.

BACKGROUND ART

An asymmetric azine compound shown by the following formula (A) has been known as a liquid crystalline compound.

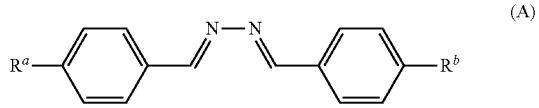
(A)

wherein $R^a$ represents an alkyl group, and $R^b$ represents an alkyl group, a cyano group, a fluorine atom, a trifluoromethoxy group, or the like.

The above asymmetric azine compound is a liquid crystal material that shows a liquid crystal phase over a wide temperature range, is relatively chemically stable, and can be produced inexpensively, for example.

The above asymmetric azine compound may be produced by (i) reacting a first aldehyde compound with hydrazine to prepare a hydrazone, and reacting the resulting hydrazone with a second aldehyde compound (Patent Document 1), or (ii) reacting an aldehyde shown by the following formula (B) with a large excess of hydrazine in an alcohol solvent to obtain a reaction solution including a hydrazone compound shown by the following formula (C),

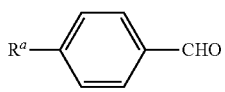
(B)

wherein $R^a$ is the same as defined above,

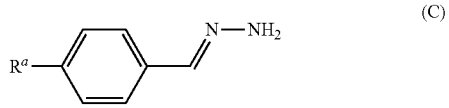
(C)

wherein $R^a$ is the same as defined above, isolating the hydrazone compound shown by the formula (C) from the reaction solution, and reacting the hydrazone compound with an aldehyde shown by the following formula (D) to obtain an asymmetric azine compound shown by the formula (A) (Patent Document 2), for example.

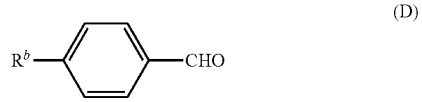
(D)

wherein $R^b$ is the same as defined above.

However, when producing an asymmetric azine compound that includes a polar group (e.g., hydroxyl group or carboxyl group) in the molecule, since the hydrazone compound (intermediate) has high water solubility, it may be difficult to isolate the hydrazone compound from the reaction system. This makes it difficult to directly apply the method disclosed in Patent Document 1 or 2.

Patent Document 2 refers to a problem that may occur when using the method disclosed in Patent Document 1. Specifically, Patent Document 2 describes that the target product may not be obtained in high yield due to a disproportionation reaction when using the method disclosed in Patent Document 1.

It is known that a disproportionation reaction is promoted by an acid. Specifically, a disproportionation reaction more easily progresses when a polar group (e.g., hydroxyl group or carboxyl group) is present in the molecule. Therefore, it is difficult to produce an asymmetric azine compound that includes a polar group (e.g., hydroxyl group or carboxyl group) in the molecule in high yield.

This problem may be solved by utilizing an aldehyde compound in which a polar group is protected by an appropriate protecting group. In this case, the reaction selectivity can be improved. However, this method is not industrially advantageous from the viewpoint of production cost due to the use of an expensive protecting group.

RELATED-ART DOCUMENT

Patent Document

Patent Document 1: JP-A-54-87688
Patent Document 2: JP-A-10-59919

DISCLOSURE OF THE INVENTION

Problems to be Solved by the Invention

The present invention was conceived in view of the above situation. An object of the present invention is to provide a method of industrially advantageously producing an asymmetric azine compound that includes a polar group (e.g., hydroxyl group or carboxyl group) in the molecule, and a novel asymmetric azine compound obtained by this method.

Means for Solving the Problems

The inventors of the present invention conducted extensive studies in order to achieve the above object. Surprisingly, the inventors found that the target asymmetric azine compound can be produced with high selectivity in high yield by reacting hydrazine and benzaldehyde that has an acidic group (e.g., hydroxyl group or carboxyl group) at the 4-position in a molar ratio of 1:1 in an alcohol solvent to precipitate a hydrazone compound to obtain a reaction solution including the hydrazone compound, adding 4-hydroxybenzaldehyde to the reaction solution without isolating the hydrazone compound from the reaction solution, and reacting the compounds. The inventors also found that a highly pure asymmetric azine compound can be isolated by easy filtration since the target asymmetric azine compound preferentially precipitates from the reaction system with the progress of the reaction. These findings have led to the completion of the present invention.

A first aspect of the present invention provides the following asymmetric azine compounds (see (1) to (3)).

(1) An asymmetric azine compound shown by the following general formula (I), (I)

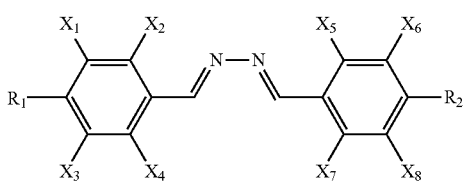

wherein $R_1$ and $R_2$ individually represent a hydroxyl group or a carboxyl group, $X_1$ to $X_8$ individually represent a hydrogen atom, a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—N($R^4$)($R^5$), or —O—C(=O)—N($R^4$)($R^5$), $R^3$, $R^4$, and $R^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —$NR^6$—C(=O)—, —C(=O)—$NR^6$—, —$NR^6$—, or —C(=O)— (excluding a case where the alkyl group is bonded via two or more adjacent —O— or —S—), and $R^6$ represents a hydrogen atom or an alkyl group having 1 to 6 carbon atoms, provided that the group shown by the following formula (IX) is not identical with the group shown by the following formula (X), (IX)

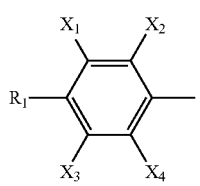

wherein $R_1$ and $X_1$ to $X_4$ are the same as defined above, (X)

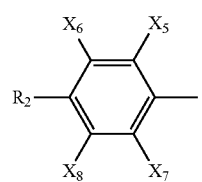

wherein $R_2$ and $X_5$ to $X_8$ are the same as defined above.

(2) An asymmetric azine compound shown by the following general formula (II), (II)

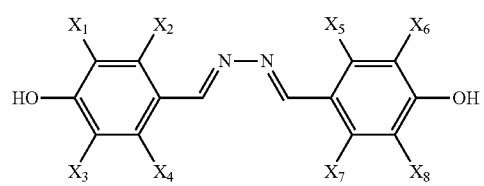

wherein $X_1$ to $X_8$ individually represent a hydrogen atom, a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—N($R^4$)($R^5$), or —O—C(=O)—N($R^4$)($R^5$), $R^3$, $R^4$, and $R^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —$NR^6$—C(=O)—, —C(=O)—$NR^6$—, —$NR^6$—, or —C(=O)— (excluding a case where the alkyl group is bonded via two or more adjacent —O— or —S—), and $R^6$ represents a hydrogen atom or an alkyl group having 1 to 6 carbon atoms, provided that the group shown by the following formula (IX) is not identical with the group shown by the following formula (X), (IX)

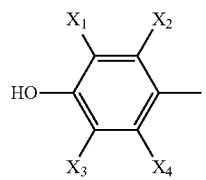

wherein $X_1$ to $X_4$ are the same as defined above, (X)

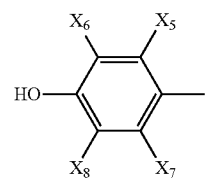

wherein $X_5$ to $X_8$ are the same as defined above.

(3) An asymmetric azine compound shown by the following general formula (II), (II)

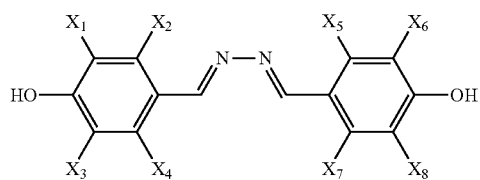

wherein $X_1$ to $X_8$ individually represent a hydrogen atom, a halogen atom, a substituted or unsubstituted alkyl group having 1 to 10 carbon atoms, a cyano group, a nitro group, —$OR^3$, —O—C(=O)—$R^3$, or —C(=O)—$OR^3$, and $R^3$ represents a hydrogen atom or a substituted or unsubstituted alkyl group having 1 to 10 carbon atoms, provided that the group shown by the following formula (IX) is not identical with the group shown by the following formula (X),

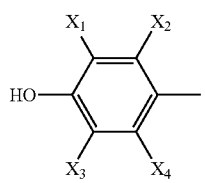

wherein $X_1$ to $X_4$ are the same as defined above,

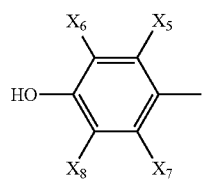

wherein $X_5$ to $X_8$ are the same as defined above.

A second aspect of the present invention provides the following methods of producing an asymmetric azine compound (see (4) to (6)).

(4) A method of producing the asymmetric azine compound according to (1), the method including reacting a compound shown by the following general formula (III) and hydrazine in a molar ratio of 2:1 to 1:2 in an alcohol solvent to obtain a reaction solution including a compound shown by the following general formula (IV),

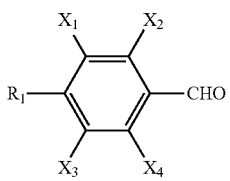

wherein $R_1$ represents a hydroxyl group or a carboxyl group, $X_1$ to $X_4$ individually represent a hydrogen atom, a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—N($R^4$)($R^5$), or —O—C(=O)—N($R^4$)($R^5$), $R^3$, $R^4$, and $R^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —$NR^6$—C(=O)—, —C(=O)—$NR^6$—, —$NR^6$—, or —C(=O)— (excluding a case where the alkyl group is bonded via two or more adjacent —O— or —S—), and $R^6$ represents a hydrogen atom or an alkyl group having 1 to 6 carbon atoms,

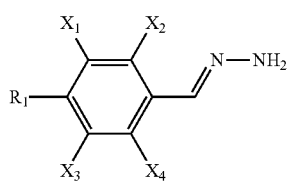

wherein $R_1$ and $X_1$ to $X_4$ are the same as defined above, adding a compound shown by the following general formula (V) to the resulting reaction solution so that the molar ratio of the compound shown by the general formula (V) to the compound shown by the general formula (IV) is 2:1 to 1:2, and reacting the compound shown by the general formula (IV) and the compound shown by the general formula (V),

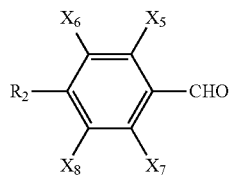

wherein $R_2$ represents a hydroxyl group or a carboxyl group, $X_1$ to $X_4$ individually represent a hydrogen atom, a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—N($R^4$)($R^5$), or —O—C(=O)—N($R^4$)($R^5$), $R^3$, $R^4$, and $R^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —$NR^6$—C(=O)—, —C(=O)—$NR^6$—, —$NR^6$—, or —C(=O)— (excluding a case where the alkyl group is bonded via two or more adjacent —O— or —S—), and $R^6$ represents a hydrogen atom or an alkyl group having 1 to 6 carbon atoms, provided that the compound shown by the general formula (III) is not identical with the compound shown by the general formula (V).

(5) A method of producing the asymmetric azine compound according to (2), the method including reacting a compound shown by the following general formula (VI) and hydrazine in a molar ratio of 2:1 to 1:2 in an alcohol solvent to obtain a reaction solution including a hydrazone compound shown by the following general formula (VII),

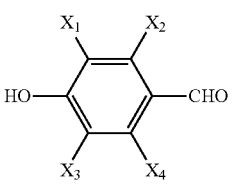

wherein $X_1$ to $X_4$ individually represent a hydrogen atom, a halogen atom, a substituted or unsubstituted alkyl group having 1 to 10 carbon atoms, a cyano group, a nitro group, —$OR^3$, —O—C(=O)—$R^3$, —C(=O)—$OR^3$, —O—C(=O)—$OR^3$, —$NR^4$—C(=O)—$R^3$, —C(=O)—N($R^4$)

($R^5$), or —O—C(=O)—N($R^4$)($R^5$), $R^3$, $R^4$, and individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —N$R^6$—C(=O)—, —C(=O)—N$R^6$—, —N$R^6$—, or —C(=O)— (excluding a case where the alkyl group is bonded via two or more adjacent —O— or —S—), and $R^6$ represents a hydrogen atom or an alkyl group having 1 to 6 carbon atoms,

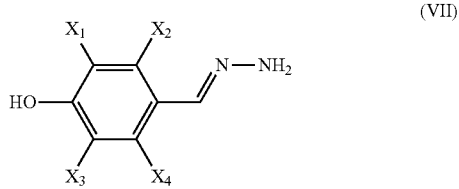

(VII)

wherein $X_1$ to $X_4$ are the same as defined above, adding a compound shown by the following general formula (VIII) to the resulting reaction solution so that the molar ratio of the compound shown by the general formula (VIII) to the compound shown by the general formula (VII) is 2:1 to 1:2, and reacting the compound shown by the general formula (VII) and the compound shown by the general formula (VIII),

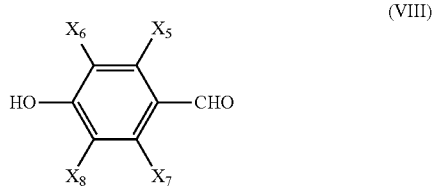

(VIII)

wherein $X_5$ to $X_8$ individually represent a hydrogen atom, a halogen atom, a substituted or unsubstituted alkyl group having 1 to 10 carbon atoms, a cyano group, a nitro group, —O$R^3$, —O—C(=O)—$R^3$, —C(=O)—O$R^3$, —O—C(=O)—O$R^3$, —N$R^4$—C(=O)—$R^3$, —C(=O)—N($R^4$)($R^5$), or —O—C(=O)—N($R^4$)($R^5$), $R^3$, $R^4$, and $R^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —N$R^6$—C(=O)—, —C(=O)—N$R^6$—, —N$R^6$—, or —C(=O)— (excluding a case where the alkyl group is bonded via two or more adjacent —O— or —S—), and $R^6$ represents a hydrogen atom or an alkyl group having 1 to 6 carbon atoms, provided that the compound shown by the general formula (VI) is not identical with the compound shown by the general formula (VIII).

(6) The method according to (4) or (5), wherein the alcohol is an alcohol having 1 to 10 carbon atoms.

Effects of the Invention

The present invention thus provides a method of industrially advantageously producing a novel asymmetric azine compound that includes a polar group (e.g., hydroxyl group or carboxyl group) in the molecule, and a novel asymmetric azine compound produced by this method.

DESCRIPTION OF EXEMPLARY EMBODIMENTS

The present invention is described in detail below.
1) Asymmetric Azine Compound The first aspect of the present invention provides an asymmetric azine compound shown by the general formula (I).

$R_1$ and $R_2$ in the general formula (I) individually represent a hydroxyl group or a carboxyl group, and preferably represent a hydroxyl group.

$X_1$ to $X_8$ individually represent a hydrogen atom, a halogen atom, a substituted or unsubstituted alkyl group having 1 to 10 carbon atoms, a cyano group, a nitro group, —O$R^3$, —O—C(=O)—$R^3$, —C(=O)—O$R^3$, —O—C(=O)—O$R^3$, —N$R^4$—C(=O)—$R^3$, —C(=O)—N($R^4$)($R^5$), or —O—C(=O)—N($R^4$)($R^5$).

Examples of the halogen atom represented by $X_1$ to $X_8$ include a fluorine atom, a chlorine atom, a bromine atom, and the like.

Examples of the substituted or unsubstituted alkyl group having 1 to 10 carbon atoms represented by $X_1$ to $X_8$ include a methyl group, an ethyl group, an n-propyl group, an isopropyl group, an n-butyl group, an isobutyl group, a sec-butyl group, a t-butyl group, an n-pentyl group, an n-hexyl group, an n-heptyl group, an n-octyl group, an n-nonyl group, an n-decyl group, and the like.

Examples of a substituent for the substituted or unsubstituted alkyl group having 1 to 10 carbon atoms represented by $X_1$ to $X_8$ include a halogen atom such as a fluorine atom and a chlorine atom; an alkoxy group such as a methoxy group and an ethoxy group; a substituted or unsubstituted phenyl group such as a phenyl group and a 4-methylphenyl group; and the like.

$R^3$ to $R^5$ individually represent a hydrogen atom or a substituted or unsubstituted alkyl group having 1 to 10 carbon atoms.

Examples of the alkyl group having 1 to 10 carbon atoms represented and a substituent for the substituted or unsubstituted alkyl group having 1 to 10 carbon atoms represented by $R^3$ to $R^5$ include the alkyl groups having 1 to 10 carbon atoms and the substituents mentioned above in connection with the substituted or unsubstituted alkyl group having 1 to 10 carbon atoms represented by $X_1$ to $X_8$.

The alkyl group represented by $R^3$, $R^4$ and/or $R^5$ may be bonded via —O—, —S—, —O—C(=O)—, —C(=O)—O—, —O—C(=O)—O—, —N$R^6$—C(=O)—, —C(=O)—N$R^6$—, —N$R^6$—, or —C(=O)— (excluding a case where the alkyl group is bonded via two or more adjacent —O— or —S—).

$R^6$ represents a hydrogen atom or an alkyl group having 1 to 6 carbon atoms, such as a methyl group, an ethyl group, an n-propyl group, an isopropyl group, an n-butyl group, an isobutyl group, a sec-butyl group, a t-butyl group, an n-pentyl, or an n-hexyl group.

Note that the group shown by the formula (IX) is not identical with the group shown by the formula (X) in the formula (I).

The asymmetric azine compound shown by the general formula (I) is preferably an asymmetric azine compound shown the general formula (II).

$X_1$ to $X_8$ in the general formula (II) are the same as defined above. It is preferable that $X_1$ to $X_8$ individually represent a hydrogen atom, a halogen atom, a substituted or unsubstituted alkyl group having 1 to 10 carbon atoms, a cyano group, a nitro group, —O$R^3$, —O—C(=O)—$R^3$, or —C(=O)—O$R^3$. $R^3$ is the same as defined above.

In the present invention, specific examples of a preferable asymmetric azine compound shown by the general formula (I) include the following compounds.
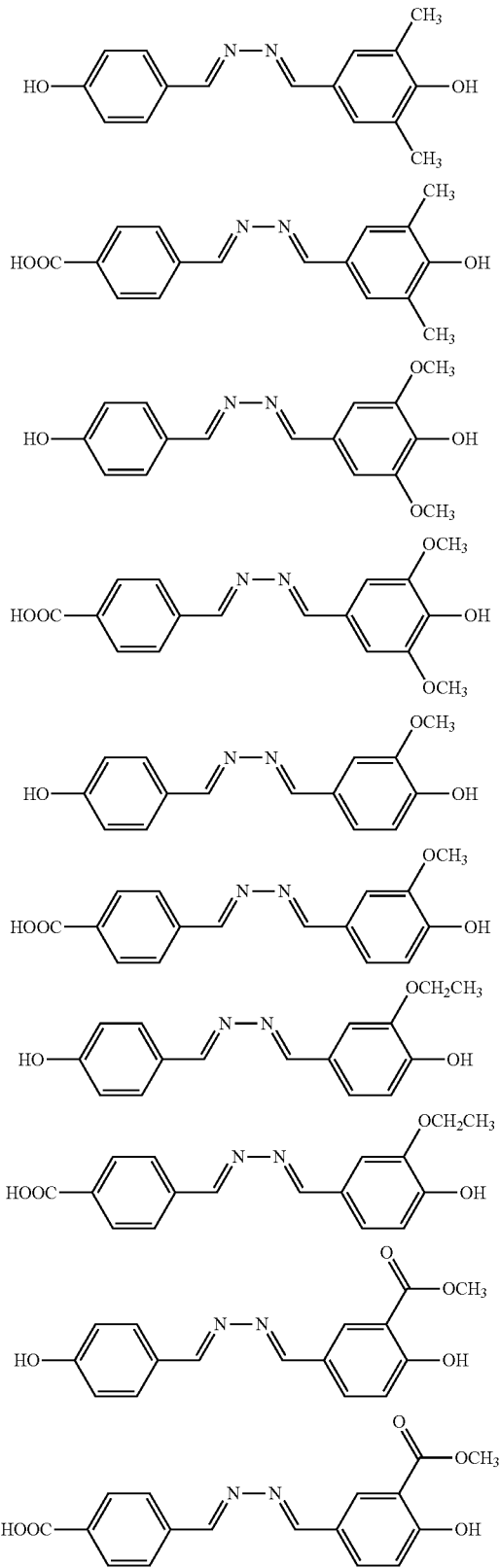
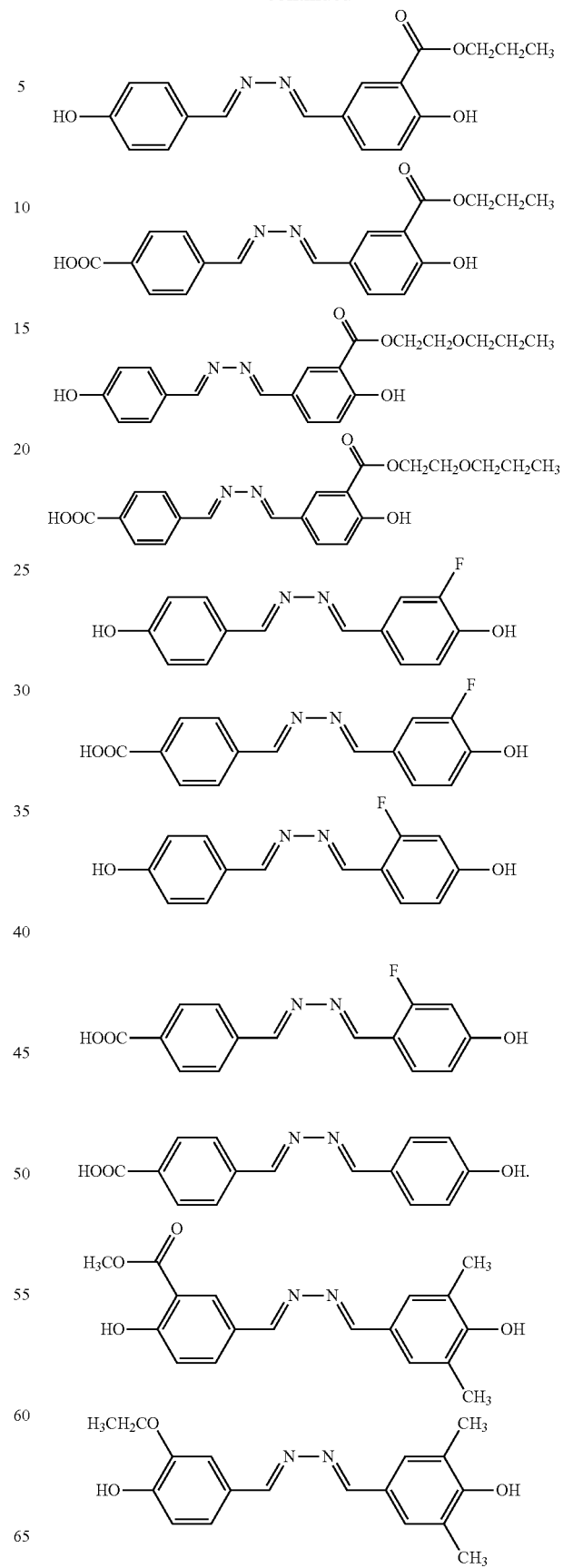

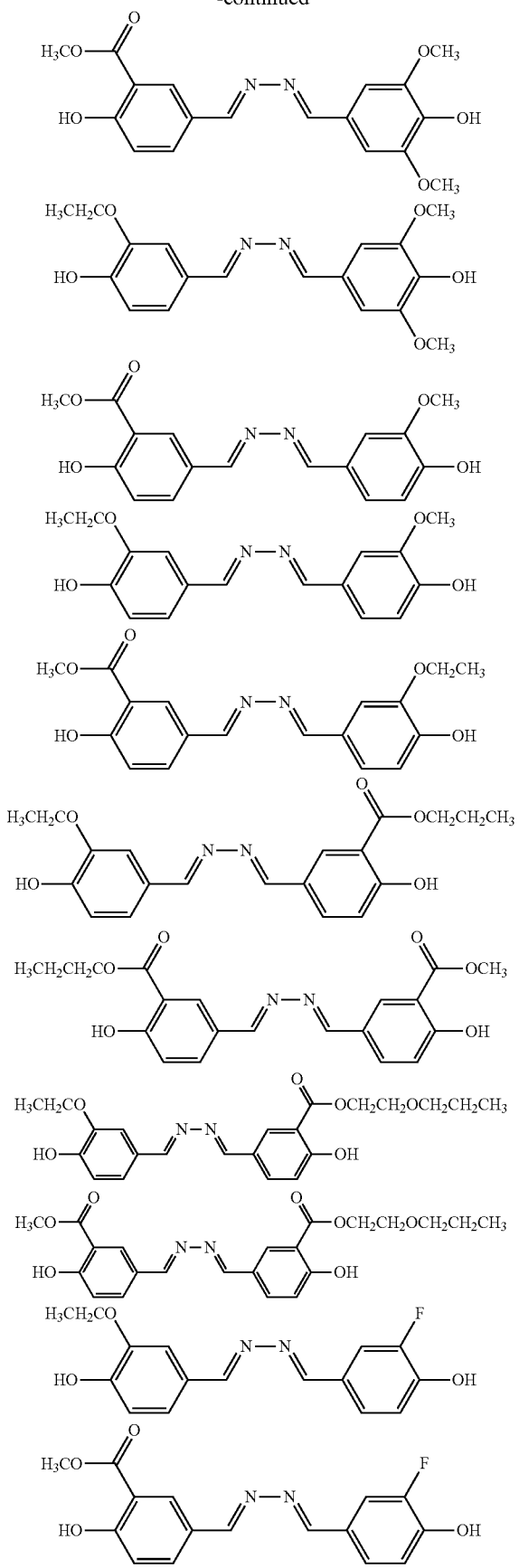

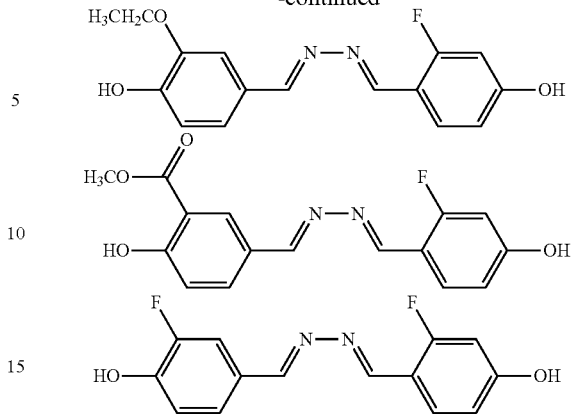

2) Method of Producing Asymmetric Azine Compound

The second aspect of the present invention provides a method of producing an asymmetric azine compound, the method comprising reacting a compound shown by the general formula (III) (hereinafter may be referred to as "aldehyde compound (III)") and hydrazine in a molar ratio of 2:1 to 1:2 in an alcohol solvent to obtain a reaction solution including a hydrazone compound shown by the general formula (IV) (hereinafter may be referred to as "hydrazone compound (IV)"), adding an aldehyde compound shown by the general formula (V) (hereinafter may be referred to as "aldehyde compound (V)") to the resulting reaction solution so that the molar ratio of the aldehyde compound (V) to the hydrazone compound (IV) is 2:1 to 1:2, and reacting the hydrazone compound (IV) and the aldehyde compound (V).

The method according to one embodiment of the present invention is schematically shown by the following reaction.

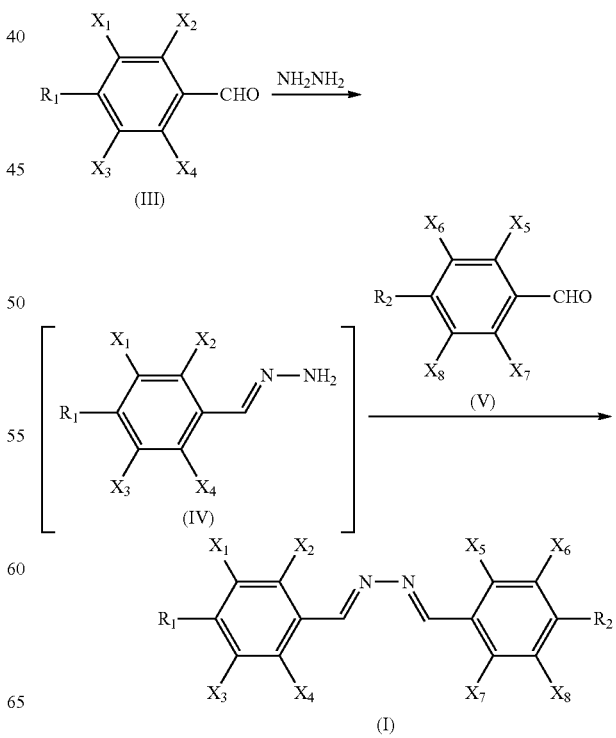

-continued

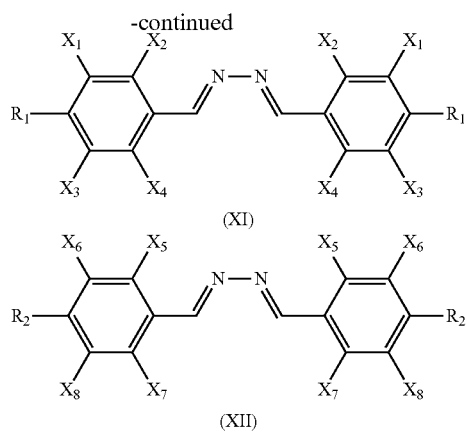

(XI)

(XII)

wherein $R_1$, $R_2$, and $X_1$ to $X_8$ are the same as defined above. The aldehyde compound (III) is not identical with the aldehyde compound (V).

As shown by the above reaction formula, the method according to one embodiment of the present invention includes reacting the aldehyde compound (III) and hydrazine in a molar ratio of 2:1 to 1:2 (preferably 1.5:1 to 1:1.5, and particularly preferably about 1:1) in an alcohol solvent to precipitate the corresponding hydrazone compound (IV) to obtain a reaction solution including the hydrazone compound (IV) (first step), adding the aldehyde compound (V) to the reaction solution without isolating the hydrazone compound (IV) from the reaction solution so that the molar ratio of the aldehyde compound (V) to the hydrazone compound (IV) is 2:1 to 1:2 (preferably 1.5:1 to 1:1.5, and particularly preferably about 1:1), and reacting the hydrazone compound (IV) and the aldehyde compound (V) (second step) to produce the target asymmetric azine compound (I) with high selectivity in high yield.

According to this method, the target asymmetric azine compound (I) can be produced with high reaction selectivity in high yield. The reaction solution obtained by the second step includes the target asymmetric azine compound (I), the azine compound (XI) produced by the reaction between two molecules of the aldehyde compound (III) and hydrazine, and the azine compound (XII) produced by the reaction between two molecules of the aldehyde compound (V) and hydrazine produced by the disproportionation reaction of the hydrazone compound (IV). However, since the target asymmetric azine compound (I) preferentially precipitates from the reaction system, as described later, a highly pure asymmetric azine compound (I) can be isolated by easy filtration. This ensures excellent operability.

Hydrazine monohydrate is normally used as hydrazine in the present invention. Commercially available hydrazine may be directly used.

The alcohol used in the present invention is not particularly limited. It is preferable to use an alcohol having 1 to 10 carbon atoms from the viewpoint of obtaining the target product with higher selectivity in high yield.

Examples of the alcohol having 1 to 10 carbon atoms include methanol, ethanol, n-propyl alcohol, isopropyl alcohol, n-butyl alcohol, isobutyl alcohol, sec-butyl alcohol, tert-butyl alcohol, n-pentyl alcohol, amyl alcohol, and the like.

The alcohol may be used in an appropriate amount taking account of the type of aldehyde compound, the type of alcohol, the reaction scale, and the like. The alcohol is normally used in an amount of 1 to 100 g per gram of hydrazine (hydrazine monohydrate).

Water may be used together with the alcohol taking account of the solubility of hydrazine, the aldehyde compound, and the hydrazone compound. An amine compound such as triethylamine may be added to the alcohol in order to improve the reaction yield.

A solvent (e.g., tetrahydrofuran) that dissolves the precipitated hydrazone compound (IV) may be used in the second step.

A known aldehyde compound may be used in the present invention, and may be prepared by a known method. A commercially available aldehyde compound may be used either directly or after purification.

Two aldehyde compounds are used in the present invention in an arbitrary order. It is preferable that an aldehyde compound that has relatively low reactivity with hydrazine be reacted with hydrazine from the viewpoint of inexpensively producing the target asymmetric azine compound (I) with high selectivity in high yield.

The reaction temperature employed in the first step and the second step is in the range from 0° C. to the boiling point of the solvent, and preferably 10 to 60° C. The reaction time is determined depending on the reaction scale, but is normally 1 minute to several hours.

After completion of the reaction, the target product may be isolated by a separation/purification means normally used in synthetic organic chemistry.

According to the present invention, since the target asymmetric azine compound (I) preferentially precipitates from the reaction system with the progress of the reaction, a highly pure asymmetric azine compound (I) can be isolated by easy filtration.

The structure of the target product may be identified by NMR spectrum analysis, IR spectrum analysis, mass spectrum analysis, gas chromatography, liquid chromatography, or the like.

EXAMPLES

The present invention is further described below by way of examples and comparative examples. Note that the present invention is not limited to the following examples.

Examples 1 to 3 and Comparative Examples 1 to 4

Synthesis of 1-(3-methoxycarbonyl-4-hydroxybenzylidene)-2-(4-hydroxybenzylidene)hydrazine

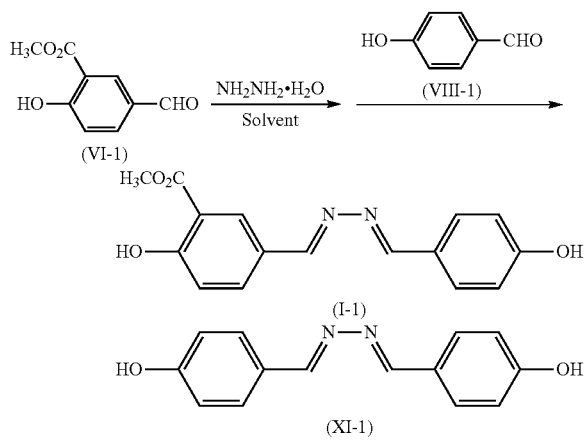

-continued

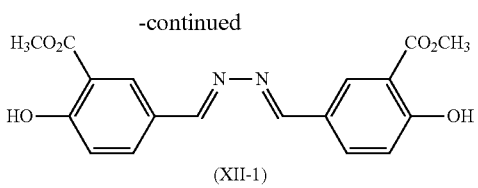

(XII-1)

The above reaction was carried out as follows.

0.5 g (10 mmol) of hydrazine monohydrate was dissolved in 20 g of a solvent shown in Table 1, and the solution was heated to a given temperature a. After the addition of 1.8 g (10 mmol) of 3-methoxycarbonyl-4-hydroxybenzaldehyde (VI-1), the mixture was stirred at the temperature a for 2 hours. After the addition of 1.22 g (10 mmol) of 4-hydroxybenzaldehyde (VIII-1), the mixture was stirred at the temperature a for 2 hours. The reaction mixture was cooled to 20° C. to sufficiently precipitate crystals. The precipitate was then filtered off to obtain a light yellow solid. The composition of the light yellow solid was analyzed by high-performance liquid chromatography.

Table 1 shows the type of solvent, the reaction temperature, the yield of the precipitate (i.e., the mixture of compounds (I-1), (XI-1), and (XII-1)), and the analysis results for the precipitate (i.e., the molar ratio of the compounds (I-1), (XI-1), and (XII-1) included in the precipitate) by high-performance liquid chromatography.

High-Performance Liquid Chromatography Conditions

The following high-performance liquid chromatography conditions were employed.
Apparatus: 1100 series manufactured by Agilent
Eluant: acetonitrile:THF:water (buffer: $KH_2PO_4$ 20 mM)=65:15:20 (volume ratio)
Column: ZORBAX Eclipse XDB-C18 (diameter: 4.6 mm, length: 250 mm) manufactured by Agilent
Temperature: 40° C.
Flow rate: 1 ml/min
Wavelength: 254 nm Symbols shown in Table 1 indicate the following.
I-PrOH: isopropyl alcohol
MeOH: methanol
DMF: N,N-dimethylformamide
THF: tetrahydrofuran

[Table 1]

TABLE 1

| | Solvent | Reaction temperature α (° C.) | Yield (g) | Compound (molar ratio) | | |
|---|---|---|---|---|---|---|
| | | | | (I-1) | (XI-1) | (XII-1) |
| Example 1 | i-PrOH | 40 | 2.2 | 70 | 5 | 25 |
| Example 2 | MeOH | 40 | 2.0 | 69 | 7 | 24 |
| Example 3 | MeOH | 23 | 2.1 | 85 | 3 | 12 |
| Comparative Example 1 | DMF | 40 | 0.6 | 10 | 1 | 90 |
| Comparative Example 2 | DMF | 23 | 0.7 | 12 | 1 | 88 |
| Comparative Example 3 | THF | 40 | 0.6 | 16 | 3 | 81 |
| Comparative Example 4 | $CH_3CN$ | 40 | 1.9 | 12 | 3 | 85 |

As shown in Table 1, when using an alcohol as the reaction solvent, the target 1-(3-methoxycarbonyl-4-hydroxybenzylidene)-2-(4-hydroxybenzylidene)hydrazine (asymmetric azine compound) was obtained with high reaction selectivity in high yield as compared with the case of using DMF (amide solvent) (Comparative Examples 1 and 2), THF (ether solvent) (Comparative Example 3), or acetonitrile ($CH_3CN$) (Comparative Example 4) as the reaction solvent.

Comparative Example 5

Synthesis of 1-(3-methoxycarbonyl-4-hydroxybenzylidene)-2-(4-hydroxybenzylidene)hydrazine 1-(3-Methoxycarbonyl-4-hydroxybenzylidene)-2-(4-hydroxybenzylidene)hydrazine was synthesized in accordance with Example 1 of Patent Document 2 using 3-methoxycarbonyl-4-hydroxybenzaldehyde and 4-hydroxybenzaldehyde. However, no product could be extracted with dichloromethane. Therefore, the target product (asymmetric azine compound) was not obtained.

INDUSTRIAL APPLICABILITY

The asymmetric azine compound according to the present invention is useful as an intermediate for a liquid crystal compound having high optical anisotropy (An). In particular, the asymmetric azine compound according to the present invention is useful as an intermediate for a novel polymerizable liquid crystal compound disclosed in PCT/JP2008/57896 (WO2008/133290).

The invention claimed is:

1. An asymmetric azine compound shown by the following general formula (II-1),

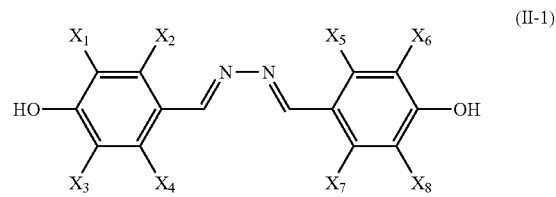

wherein $X_1$ represents —C(=O)—$OR^3$, $R^3$ represents a hydrogen atom or a substituted or unsubstituted alkyl group having 1 to 10 carbon atoms, and $X_2$ to $X_8$ represent a hydrogen atom.

2. The asymmetric azine compound according to claim 1, wherein $X_1$ represents —C(=O)—$OCH_3$.

3. A method of producing an asymmetric azine compound shown by the following general formula (II), the method comprising reacting a compound shown by the following general formula (VI) and hydrazine in a molar ratio of 2:1 to 1:2 in an alcohol solvent to obtain a reaction solution including a hydrazone compound shown by the following general formula (VII),

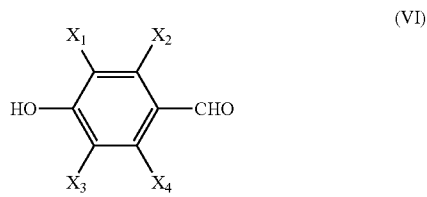

wherein $X_1$ to $X_4$ individually represent a hydrogen atom, a halogen atom, a substituted or unsubstituted alkyl group having 1 to 10 carbon atoms, a cyano group, a nitro group, —OR$^3$, —O—C(=O)—R$^3$, —C(=O)—OR$^3$, —O—C(=O)—OR$^3$, —NR$^4$—C(=O)—R$^3$, —C(=O)—N(R$^4$)(R$^5$), or —O—C(=O)—N(R$^4$)(R$^5$), R$^3$, R$^4$, and R$^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —NR$^6$—C(=O)—, —C(=O)—NR$^6$—, —NR$^6$—, or —C(=O)— (excluding a case where the alkyl group is bonded via two or more adjacent —O— or —S—), and R$^6$ represents a hydrogen atom or an alkyl group having 1 to 6 carbon atoms,

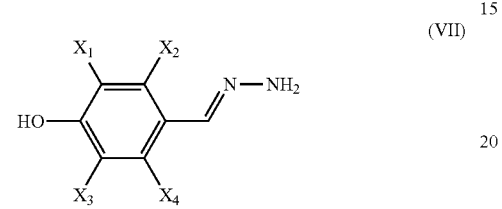

(VII)

wherein $X_1$ to $X_4$ are the same as defined above, adding a compound shown by the following general formula (VIII) to the resulting reaction solution so that the molar ratio of the compound shown by the general formula (VII) to the compound shown by the general formula (VII) is 2:1 to 1:2, and reacting the compound shown by the general formula (VII) and the compound shown by the general formula (VIII),

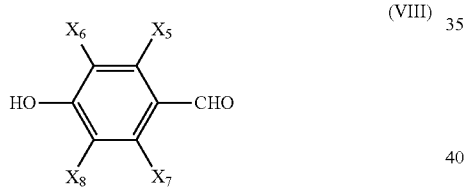

(VIII)

wherein $X_5$ to $X_8$ individually represent a hydrogen atom, a halogen atom, a substituted or unsubstituted alkyl group having 1 to 10 carbon atoms, a cyano group, a nitro group, —OR$^3$, —O—C(=O)—R$^3$, —C(=O)—OR$^3$, —O—C(=O)—OR$^3$, —NR$^4$—C(=O)—R$^3$, —C(=O)—N(R$^4$)(R$^5$), or —O—C(=O)—N(R$^4$)(R$^5$), R$^3$, R$^4$, and R$^5$ are the same as defined above, provided that the compound shown by the general formula (VI) is not identical with the compound shown by the general formula (VIII),

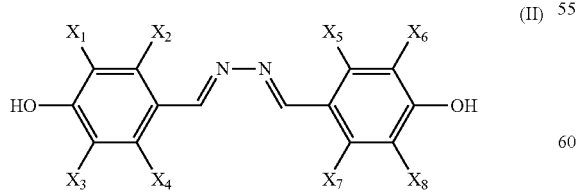

(II)

wherein $X_1$ to $X_8$ are the same as defined above, provided that the group shown by the following formula (IX) is not identical with the group shown by the following formula (X),

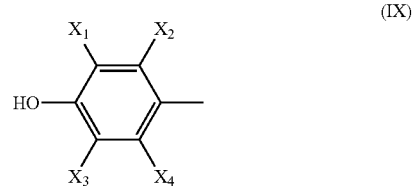

(IX)

wherein $X_1$ to $X_4$ are the same as defined above,

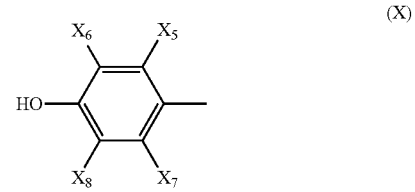

(X)

wherein $X_5$ to $X_8$ are the same as defined above, wherein the alcohol is an alcohol having 1 to 10 carbon atoms.

4. A method of producing an asymmetric azine compound shown by the following general formula (II), the method comprising reacting a compound shown by the following general formula (VI) and hydrazine in a molar ratio of 2:1 to 1:2 in an alcohol solvent to obtain a reaction solution including a hydrazone compound shown by the following general formula (VII),

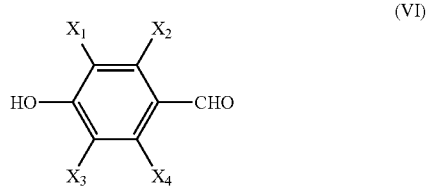

(VI)

wherein $X_1$ to $X_4$ individually represent a hydrogen atom, a halogen atom, a substituted or unsubstituted alkyl group having 1 to 10 carbon atoms, a cyano group, a nitro group, —OR$^3$, —O—C(=O)—R$^3$, —C(=O)—OR$^3$, —O—C(=O)—OR$^3$, —NR$^4$—C(=O)—R$^3$, —C(=O)—N(R$^4$)(R$^5$), or —O—C(=O)—N(R$^4$)(R$^5$), R$^3$, R$^4$, and R$^5$ individually represent a hydrogen atom or a substituted or unsubstituted alkyl group having 1 to 10 carbon atoms that may be bonded via —O—, —S—, —O—C(=O)—, —C(=O)—O—, —O—C(=O)—O—, —NR$^6$—C(=O)—, —C(=O)—NR$^6$—, —NR$^6$—, or —C(=O)— (excluding a case where the alkyl group is bonded via two or more adjacent —O— or —S—), and R$^6$ represents a hydrogen atom or an alkyl group having 1 to 6 carbon atoms,

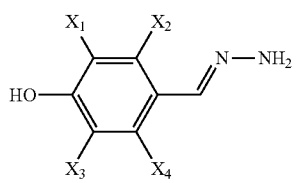

(VII)

wherein $X_1$ to $X_4$ are the same as defined above, adding a compound shown by the following general formula (VIII) to the resulting reaction solution so that the molar ratio of the compound shown by the general formula (VIII) to the compound shown by the general formula (VII) is 2:1 to 1:2, and reacting the compound shown by the general formula (VII) and the compound shown by the general formula (VIII),

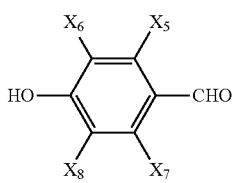

(VIII)

wherein $X_5$ to $X_8$ individually represent a hydrogen atom, a halogen atom, a substituted or unsubstituted alkyl group having 1 to 10 carbon atoms, a cyano group, a nitro group, $-OR^3$, $-O-C(=O)-R^3$, $-C(=O)-OR^3$, $-O-C(=O)-OR^3$, $-NR^4-C(=O)-R^3$, $-C(=O)-N(R^4)(R^5)$, or $-O-C(=O)-N(R^4)(R^5)$, $R^3$, $R^4$, and $R^5$ are the same as defined above, provided that the compound shown by the general formula (VI) is not identical with the compound shown by the general formula (VIII),

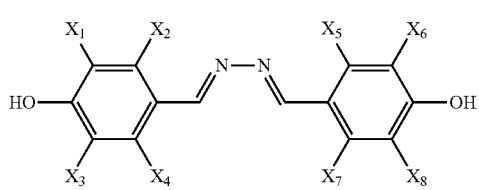

(II)

wherein $X_1$ to $X_8$ are the same as defined above, provided that the group shown by the following formula (IX) is not identical with the group shown by the following formula (X),

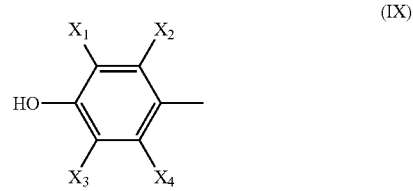

(IX)

wherein $X_1$ to $X_4$ are the same as defined above,

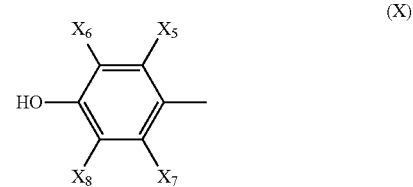

(X)

wherein $X_5$ to $X_8$ are the same as defined above, wherein $X_1$ represents $-C(=O)-OR^3$, $R^3$ represents a hydrogen atom or a substituted or unsubstituted alkyl group having 1 to 10 carbon atoms, and $X_2$ to $X_8$ represent a hydrogen atom, wherein the alcohol is an alcohol having 1 to 10 carbon atoms.

\* \* \* \* \*